United States Patent [19]
Harris
[11] Patent Number: 4,504,412
[45] Date of Patent: Mar. 12, 1985

[54] CYCLOHEXANE DERIVATIVES IN FRAGRANCE COMPOSITIONS

[75] Inventor: Eugene G. Harris, West Chester, Ohio

[73] Assignee: National Distillers and Chemical Corporation, New York, N.Y.

[21] Appl. No.: 464,533

[22] Filed: Feb. 7, 1983

[51] Int. Cl.$^3$ ........ A61K 7/46
[52] U.S. Cl. ........ 252/522 R; 560/231
[58] Field of Search ........ 560/231; 252/522 R

[56] References Cited

PUBLICATIONS

Zeinalov et al., "C.A.", vol. 67 (1967) 73198p.

*Primary Examiner*—Anton H. Sutto
*Attorney, Agent, or Firm*—Kenneth D. Tremain; Gerald A. Baracka

[57] ABSTRACT

Fragrance compounds having the formula

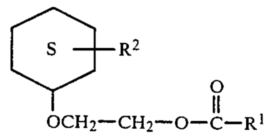

wherein $R^1$ is hydrogen or lower alkyl and $R^2$ is hydrogen or lower alkyl.

6 Claims, No Drawings

CYCLOHEXANE DERIVATIVES IN FRAGRANCE COMPOSITIONS

BACKGROUND OF THE INVENTION

This invention relates to fragrance compositions and more particularly to a novel class of compounds useful as fragrances or as components in fragrance compositions.

While many natural perfume chemicals, such as essential oils, like, oil of rose and oil of cloves, and animal secretions, such as musk, are known, a large number of synthetic odoriferous chemicals possessing aroma characteristics have been developed. Synthetic aroma chemicals have added a new dimension to the art of perfuming, since these synthetics are usually stable compounds and are relatively inexpensive, as compared with the natural perfume chemicals. Moreover, synthetics lend themselves more easily to manipulation than natural perfume chemicals since natural perfume chemicals are usually a complex mixture of substances which defy chemical analysis. Accordingly, for these and other reasons, there is a great desire in the art of fragrance chemistry fornewcompounds possessing specific characteristic aromas.

SUMMARY OF THE INVENTION

Accordingly, it is one object of the present invention to provide a novel class of fragrance compounds.

Another object of this invention is to provide a fragrance composition utilizing novel synthetic aroma compounds.

Still another object of the present invention is to provide novel aroma compounds utilized in the preparation of fragrances and fragrance compositions.

These and other objects are achieved herein by providing a novel class of cyclohexane derivatives having the general structural formula (I)

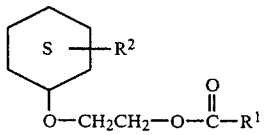

wherein $R^1$ is hydrogen or a lower alkyl having from 1 to 10 and, more preferably 1 to 4, carbon atoms and $R^2$ is hydrogen or lower alkyl having from 1 to 4 carbon atoms. For the purposes of the present invention, a preferred compound within the above structure is 2-cyclohexoxyethylisobutyrate which has a natural, sweet, floral odor. Another preferred compound corresponding to the above formula is 2-(4-methylcyclohexoxy)ethylacetate which has a natural, fruity odor.

DETAILED DESCRIPTION OF THE INVENTION

The novel compounds of the present invention are represented by general formula I. The odor of these compounds will vary depending on the ring substituent and the ester moiety. Representative alkyl groups for $R^1$ in the above general formula I include methyl, ethyl, n-propyl, isopropyl, n-butyl, isobutyl, tert-butyl, n-amyl, iso-amyl, tert-amyl, n-octyl, n-nonyl, etc. Representative alkyl groups for $R^2$ include methyl, ethyl, n-propyl, tert-butyl and the like.

Specific compounds included within formula I hereinabove include 2-cyclohexoxyethylformate, 2-cyclohexoxyethylacetate; 2-cyclohexoxyethylpropionate; 2-cyclohexoxyethylisobutyrate; 2-(4-methylcyclohexoxyethylformate; 2-(4-methylcyclohexoxy)ethylacetate; 2-(4-methylcyclohexoxy)ethylisobutyrate; 2-(4-t-butylcyclohexoxy)ethylformate; 2-(4-ethylcyclohexoxy)ethylacetate; 2-(4-isopropylcyclohexoxy)ethylacetate; 2-(4-t-butylcyclohexoxy)ethylacetate; 2-(4-t-butylcyclohexoxy)ethylacetate; 2-(4-t-butylcyclohexoxy)ethylisobutyrate; and the like.

Particularly useful cyclohexane derivatives, in view of their highly desirable odor characteristics, are 2-cyclohexoxyethylisobutyrate and 2-(4-methylcyclohexoxy)ethylacetate. The former compound has a natural, sweet, floral odor while the latter has a natural, fruity odor. These compounds, as well as other cyclohexane derivatives of this invention are useful as components in the formulation of fragrance compositions.

The novel cyclohexane derivatives of the present invention are generally prepared by hydrogenation of the appropriate 2-phenoxyethylacylate. This reaction is illustrated as follows:

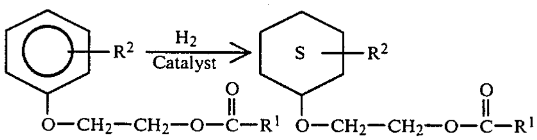

wherein $R^1$ and $R^2$ are as defined hereinabove. The hydrogenation step may be carried out in accordance with conventional hydrogenation conditions and in the presence of conventional hydrogenation catalysts. Typical hydrogenation catalysts, include those which customarily contain Group VIII metals or compounds thereof. The Group VIII metals are preferably noble metals selected from the group consisting of ruthenium, rhodium, palladium and platinum are preferred and rhodium is especially useful. The catalyst may contain at least one noble metal although the combined use of two metals is within the scope herein. These hydrogenation catalysts may be used in various forms, such as, for example, sponge, fine powder, colloid and supported. Active carbon, alumina, silica, silica-alumina, boria, tungsten trioxide, molybdenum trioxide, zeolites, asbestos, other known solid acidic supports and cation exchange resins may be used as a carrier for a supported catalyst. An alloy of the noble metal with other metals such as copper, silver and gold may also be used.

The quality of the hydrogen gas used in the hydrogenation reaction is not critical except that the hydrogen gas should not contain impurities which tend to poison the hydrogenation catalyst or otherwise detract from its activity. The hydrogen may contain an inert gas, such as nitrogen, helium, argon, carbon dioxide or methane.

The hydrogen pressure employed is not critical either. Preferably, a partial pressure of hydrogen in the range of from about 30 psi to about 150 psi, preferably from about 30 psi to about 60 psi is used. The hydrogenation reaction temperature is generally in the range offrom about 20° C. to about 100° C., preferably from about 25° C. to about 50° C. Moreover, the reaction may be carried out in an inert solvent, such as, for example, methanol, dioxane, cyclohexane, n-octane, etc.

The 2-phenoxyethylacylate starting materials from which the cyclohexane derivatives of the present invention are prepared are either commercially available or can be prepared according to the following scheme:

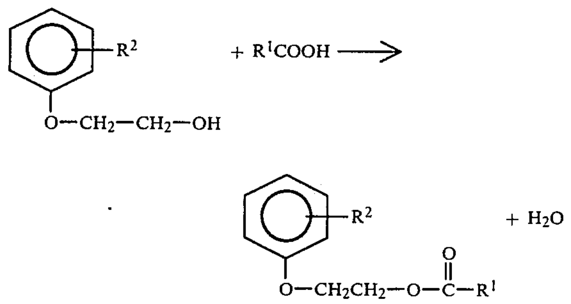

wherein $R^1$ and $R^2$ are as defined hereinabove. Generally the above reaction is carried out under typical esterification reaction conditions which facilitate the preparation of the desired product.

This generally involves reacting a molar excess of the monocarboxylic acid with the 2-phenoxyethanol at an elevated temperature while removing water. The reaction may be carried out by refluxing the reactants in an azeotroping solvent, such as toluene or xylene, to facilitate removal of the water. Catalysts such as mineral acids and metal compounds, such as stannous oxalate, may be used to increase the rate of esterification but are not essential to obtain esterification. Upon completion of the reaction any excess acid and remaining solvent are separated from the ester by vacuum stripping or distillation. The desired 2-phenoxyethylacylates may also be obtained using established transesterification procedures.

The cyclohexane derivatives can also be obtained using other preparative methods. One such method would be to hydrogenate the ethylene glycol ketal of cyclohexane or an alkyl-substituted cyclohexane in accordance with the following equation:

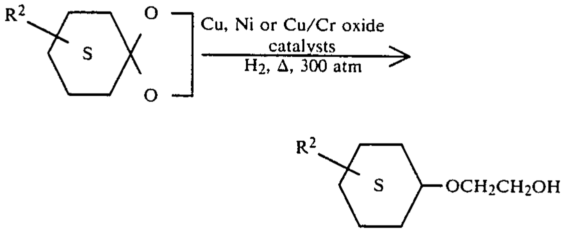

where $R^2$ is as defined above. The ester can then be obtained by reaction with a $C_{1-4}$ monocarboxylic acid.

As a result of their pleasing, strong and long lasting aroma, the novel 2-cyclohexoxyethylesters of the present invention are useful components in the preparation and formulation of fragrance compositions, such as perfumes and perfumed products. Perfume compositions and the use thereof in cosmetic, detergent and bar soap formulations and the like are exemplary of the utility thereof.

The compounds of this invention can be used in concentrations of from trace amounts up to about 30 percent of the fragrance composition into which they are incorporated. As will be expected, the concentration of the compound will vary depending on the particular fragrance desired in the composition and even within the same composition when compounded by different perfumers.

The following examples are presented by way of illustration and not by way of limitation so that those skilled in the art may better understand how to practice the present invention.

EXAMPLE 1

Reagents:

1. 2-Phenoxyethanol—138 g (1 mole)
2. Itobutyric acid—150 ml. (1.6 mole)

The reagents are mixed in a 500 ml. flask equipped with a magnetic stirrer, heating mantle, and a Dean-Stark trap with a condenser and thermometer. The mixture is heated for 2 hours. Gas chromatographic (G.C.) analysis shows about 50% conversion and therefore 1 ml of $H_2SO_4$ is added. After 1 hour a total of 20 ml of water has been collected. G.C. analysis shows less than 1% 2-phenoxyethanol still present, and the reaction mixture is poured into about 150 ml of 2N KOH, shaken and separated. The product is passed through a filter of basic Alumina to give a light yellow-brown material. G.C. analysis shows 4.8% 2-phenoxyethanol, 88.2% 2-phenoxyethylisobutyrate, and 4.9% di-ethoxylated material. The product is slurried with 25 g basic Alumina for ½ hour to give a light yellow product. G.C. analysis shows 3.9% phenoxyethanol, 90.1% 2-phenoxyethylisobutyrate and 4.8% diethoxylated product.

EXAMPLE 2

Reagents:

1. 2-Phenoxyethanol—138 g (1 mole)
2. Isobutyric Acid—130 ml (1.4 mole)

The reagents are mixed with a small amount of stannous oxalate catalyst in a 500 ml. flask equipped with a Dean-Stark trap with a condenser and thermometer, magnetic stirrer, and heating mantle. The mixture is brought to reflux. After 2 hours, 15.5 ml. of $H_2O$ has been collected and a G.C. shows 6.2% 2-phenoxyethanol and 87.2% product. After 3 hours, 20 ml. of $H_2O$ has been collected and a G.C. shows 90.1% product and no 2-phenoxyethanol. Part of the material is filtered thru basic alumina and part thru filter paper. The material that passes thru the alumina is clearer and had less color, but the G.C. analysis of the materials is identical. G.C. analysis shows no 2-phenoxyethanol, 88% 2-phenoxyethylisobutyrate, 5% diethoxylated product and 6% unknown. The product is washed twice with $H_2O$, dried with $Na_2SO_4$ and distilled to 98+% purity.

EXAMPLE 3

10.4 Grams (0.05 moles) of the 2-phenoxyethylisobutyrate, prepared according to Examples 1 or 2 and 100 ml of absolute methanol are charged to Parr shaker glass bottle. $N_2$ is bubbled thru the system for ½ hour. 1.5 Grams of 5% rhodium on alumina are then added to the bottle. The Parr shaker apparatus is purged twice with $H_2$, then pressurized with hydrogen to 30 psi for about two hours.

G.C. confirms the reaction product to be 81.0% 2-cyclohexoxyethylisobutyrate. There is 17% by-product present. The product is distilled using 30-plate micro-still. 8.4 gm is charged to a 25 ml flask. 4.2 Grams product, 99.0% pure, having a sweet, natural, floral odor is recovered. Nuclear magnetic resonance spectroscopic analysis (NMR) confirms the structure of the hydrogenated product to be

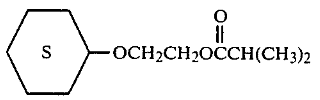

Infrared analysis (IR) confirms the presence of C=0 strech (ester) at 1725 $cm^{-1}$.

EXAMPLE 4

300 Grams (2.00 moles) of 4-t-butylphenol, 0.56 gm (.01 moles) of crushed KOH and 0.59 gm (0.015 moles) of sodium borohydride are charged to 1 liter Parr autoclave and heated to 125° C. under $N_2$. 98 Grams (2.23 moles) of ethylene oxide are charged to a pressurized addition funnel. The material in the autoclave is heated to 140° C. and the addition of the ethylene oxide is started. The mixture is heated at 130° C. for 2 hours 15 minutes. G.C. samples are taken during this time in order to determine percent phenol. After 2 hours and 15 minutes, percent phenol is 0.132%. The autoclave is cooled to 80° C., then $N_2$ is blown through for 10 minutes and cooled to room temperature. The reaction mixture is distilled through a 12" Vigreaux column and 283.68 gm of white liquid, whose G.C. shows 98.8% 2-(4-t-butylphenoxy)ethanol, is recovered.

50 Grams (0.26 moles) of 2-(4-t-butylphenoxy)ethanol (prepared above), 25.5 gm (0.29 moles, 26.8 ml) of isobutyric acid, 0.8 gm of Amberlyst 15 and 100 ml toluene are charged to a 250 ml flask fitted with magnetic stirrer, Dean-Stark trap and Friedrick condenser. The mixture is heated to reflux for 9.5 hours until the theoretical amount of water is removed (5 ml). The Amberlyst is filtered off and then the solvent is removed by evaporation. G.C. analysis of this crude mixture shows 81.3% product. The reaction mixture is distilled through a 6" Vigreaux column. The first cut is discarded and G.C. analysis shows 95% 2-(4-t-butylphenoxy)ethylisobutyrate. IR confirms the product structure.

15 Grams (0.06 moles) of 2-(4-t-butylphenoxy)ethylisobutyrate (prepared above) and 100 ml. of methanol are charged to a Parr shaker bottle. $N_2$ is bubbled through for 15 minutes. 1.5 Grams of 5% rhodium on carbon are added and the system is purged three times with $H_2$. A hydrogen pressure of 30 psi is then maintained for approximately 18 hours. The solution is filtered twice through dicalite to remove catalyst and the solvent is removed by evaporation. G.C. and IR analysis indicates product to be 2-(4-t-butylcyclohexoxy)ethylisobutyrate (74.9%).

EXAMPLE 5

250 Grams (2.31 moles) of 4-methylphenol (p-cresol), 0.62 gm (0.011 moles) of crushed KOH and 0.66 gm (0.017 moles) of sodium borohydride are charged to a 1 liter Parr autoclave and heated to 130° C. under $N_2$. 114 Grams (2.58 moles) of ethylene oxide are charged to a pressurized addition funnel and the addition of ethylene oxide is started with temperature kept in 130°-140° C. range and pressure between 30-40 psig. Addition is completed after 40 minutes. The mixture is heated for ½ hour after which a sample is removed for G.C. analysis. G.C. analysis shows no starting cresol, 92.3% monoethoxylated product and 7.8% diethoxylated product. The heating is continued 45 minutes after a sample is taken while the G.C. is run. Autoclave cooled to 80° C., then $N_2$ blown through for 10 minutes and cooled to room temperature. The reaction mixture is distilled through 12" Vigreaux column and 261.06 gm of white crystals whose G.C. shows 100% product - 2-(4-methylphenoxy)ethanol.

20 Grams (0.13 moles) of 2-(4-methylphenoxy)ethanol (prepared above) and 100 ml of dry methanol are charged to a Parr shaker bottle. $N_2$ is bubbled through for 15 minutes. 2 Grams of 5% rhodium on carbon are then added and the shaker bottle set in a Parr apparatus. The system is purged three times with $H_2$ and then pressurized to 30 psi. Hydrogen is periodically added over a period of about 20 hours up to a maximum pressure of 30 psi. The catalyst is then filtered off over dicalite and methanol is removed by evaporation. The product is distilled utilizing a 4" glass column packed with glass beads to obtain 80.9% 2-(4-methylcyclohexoxy)ethanol product.

5.65 Grams (0.04 moles) of 2-(4-methylcyclohexoxy)ethanol (prepared above), 0.8 gm of Amberlyst 15 and 100 ml. of acetic anhydride are charged to a 250 ml flask fitted with a magnetic stirrer and Friedrick condenser. The mixture is heated at reflux for 1½hours, filtered, and acetic anhydride removed by evaporation. The mixture is distilled and 7.92 gms of 2-(4-methylcyclohexoxy)ethylacetate obtained. The structure of the 2-(4-methylcyclohexoxy)ethylacetate is confirmed by NMR. The 2-(4-methylcyclohexoxy)ethylacetate has an extremely pleasant natural, fruity, wine-like odor.

Obviously, other modifications and variations of the present invention are possible in light of the above teachings. It is therefore to be understood that changes may be made in the particular embodiments of this invention which are within the full intended scope of the invention as defined by the appended claims.

I claim:

1. A fragrance composition having incorporated therein an odoriferous amount of a compound having the general structural formula:

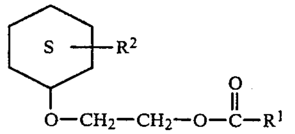

wherein $R^1$ is hydrogen or a lopwer alkyl having from 1 to about 10 carbons and $R^2$ is selected from the group consisiting of hydrogen and lower alkyl having from 1 to about 4 carbon atoms providing a pleasing, strong and long lasting aroma.

2. A fragrance composition having incorporated therein an odoriferous amount of 2-cyclohexoxyethylisobutyrate providing a natural, sweet, floral odor.

3. A fragrance composition having incorporated therein an odoriferous amount of 2-(4-methylcyclohexoxy) ethylacetate providing a natural, fruity, wine-like odor.

4. A process for providing a fragrance composition comprising incorporating therein an odoriferous amount of a compound having the structural formula:

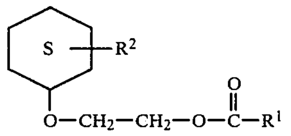

wherein $R^1$ is hydrogen or a lower alkyl having from 1 to about 10 carbons and $R^2$ is selected from the group consisting of hydrogen and lower alkyl having from 1 to 4 carbon atoms providing a pleasing, strong and long lasting aroma.

5. The process for providing a fragrance composition comprising incorporating therein an odoriferous amount of 2-cyclohexoxyethylisobityate providing a natural, sweet, floral odor.

6. The process for providing a fragrance composition comprising incorporating therein as odoriferous amount of 2-(4-methylcyclohexoxy) ethylacetate providing a natural, fruity, wine-like odor.

* * * * *